United States Patent [19]

Calvin et al.

[11] 4,162,309

[45] Jul. 24, 1979

[54] WATER SOLUBLE EXTRACTS OF CERTAIN MARINE RED ALGAE AND PROCESSES FOR USE THEREOF

[76] Inventors: Natasha I. Calvin; Robert J. Ellis, both of Box 112, Auke Bay, Ak. 99821

[21] Appl. No.: 894,833

[22] Filed: Apr. 10, 1978

[51] Int. Cl.² .................. A61K 35/78; A61K 31/70
[52] U.S. Cl. .............................. 424/195; 424/180
[58] Field of Search .............................. 424/195

[56] References Cited

FOREIGN PATENT DOCUMENTS

| 45-20953 | 7/1970 | Japan | 424/195 |
| 48-18446 | 6/1973 | Japan | 424/195 |
| 331833 | 9/1958 | Switzerland | 424/195 |

OTHER PUBLICATIONS

Frank et al., Antimicrobial Agents & Chemotherapy, Oct. 1974, pp. 524–525, vol. 6, No. 1, published by Amer. Soc. for Microbiology.

Ehresmann et al., J. Phycol. 13, pp. 37–40 (1977) accepted Aug. 30, 1976.

Takemoto et al., Proc. Soc. Exp. Biol. and Med, vol. 116 (1964) pp. 140–144, "Herpes Virus and Acid Polysaccharides".

The Dispensatory of the U.S.A., 24th Ed. (1947) pp. 28–30, published by J. B. Lippincott Co., Phila., Pa.

*Primary Examiner*—Donald B. Moyer
*Attorney, Agent, or Firm*—Christensen, O'Connor, Johnson & Kindness

[57] ABSTRACT

A water soluble extract from marine red algae selected from the group consisting of *Neodilsea americana* and *Neodilsea integra* and mixtures thereof has been found effective to inhibit the growth of herpes simplex virus, type 1 and type 2, and herpes zoster, and to relieve the pain caused by infection attributable to such virus.

3 Claims, No Drawings

WATER SOLUBLE EXTRACTS OF CERTAIN MARINE RED ALGAE AND PROCESSES FOR USE THEREOF

BACKGROUND OF THE INVENTION

The present invention relates to water soluble extracts of certain red algae, and more particularly to the water soluble extract of the alga *Neodilsea americana* and related species of algae, and to the processes for producing an aqueous extract from the algae, as well as processes for administering the water soluble extract for the treatment of certain viral infections attributable to herpes simplex virus, type 1 and type 2 and herpes zoster.

It has been suggested that certain marine red algae found off the California coast have some inhibiting activity on the replication of types 1 and 2 herpes simplex virus (hereinafter referred to as the herpes virus). See, for example, the articles by Ehresmann, D. W., et al., "Inhibition of Herpesvirus Replication by Marine Algae Extracts," *Antimicrobial Agents and Chemotherapy*, Vol. 6, No. 1, October, 1974, pp. 524 and 525, and "Antiviral Substances from California Marine Algae," *J. Phycol.*, Vol. 13, pp. 37–40, 1977.

Although the antiviral activity of such marine red algae has been noted in literature, the antiviral activity of such algae has proven to be of limited efficacy for the inhibition of replication of the herpes virus. For instance, there has been no demonstrated effectiveness of such algae against vesicular stomatitis or for relief of pain. Studies have indicated that other marine flora and fauna may also have antiviral activity. Prior to the present discovery, however, no readily available, simply processible and usable antiviral agent has been discovered that yields a very high degree of antiviral activity with respect to the herpes virus or that relieves pain.

SUMMARY OF THE INVENTION

In accordance with the discoveries disclosed herein, it has been found that the water soluble extract of *Neodilsea americana* and *Neodilsea integra* or mixtures thereof are extremely effective for the treatment of herpes type viruses, that is, to inhibit replication of the virus. Moreover, it has surprisingly been found that such water soluble extracts are extremely effective in relieving pain caused by herpetic infections upon topical application. The water soluble extract of the aforementioned algae is also effective in treating and relieving the pain of herpetic lesions of the skin, genital herpes infections and of herpes zoster. It is also believed that the water soluble extract of the above-identified algae is effective in the prevention or treatment of varicella (chicken pox) lesions, closely related to herpes zoster, prevention or treatment of herpetic infection in the fetus or newly born child, treatment of herpetic encephalitis, and of other herpetic diseases.

DETAILED DESCRIPTION OF THE INVENTION

It has been found that a water soluble extract from the marine red alga *Neodilsea americana* Abbott is extremely effective to inhibit the replication of the herpes virus, as well as for almost immediately relieving pain caused by herpetic infections. *Neodilsea americana* has been identified in the reproductive stage in accordance with the description of Abbott. *Neodilsea americana* is indigenous to the Oregon, Washington, British Columbia, Canada, and Alaska Pacific coastal waters. In the nonreproductive stage, the alga *Neodilsea integra* is similar in appearance to *Neodilsea americana* and it is believed that in efficacy of treatment of herpes virus *N. integra* is virtually identical to and indistinguishable from *N. americana*. A water soluble extract from either of the aforementioned two red marine algae or mixtures thereof is effective to inhibit replication of the herpes virus and relieve the pain caused by herpetic infection.

There are believed to be at least two active components in the water soluble extract of the algae. One of the components is active to almost completely inhibit replication of the herpes virus. The other active component relieves the pain associated with herpetic infections. The active components, which have not been identified, are derived by aqueous extraction from the algae.

The active components can be extracted from the algae by first gathering the fresh algae from its salt water environment and washing it in clean tap or distilled water. The algae is then preferably dried at room temperature to a water content on the order of 10% by weight. The algae can be stored in air dried form or can be further dried in an oven at a relatively low, nondestructive temperature in the range of from 100° F. to 120° F., and preferably on the order of 120° F. The algae can then be comminuted by any suitable device (such as a blender, mortar and pestle, or commercially available grinders,) to a fine powder and stored for an indefinite time in dry form. The water soluble active components are extracted by mixing the algal powder with water, and maintaining contact between the powder and water with frequent stirring or shaking for on the order of 30 minutes or more. Preferably the supernatant fluid is then separated from the algal residue. The active ingredients are contained in the supernatant fluid in concentrated form. Alternatively, the algae need not be dried prior to the water extraction step, but is preferably washed free of salt water. After washing, the algae can be comminuted in its freshly washed form or can be frozen and thereafter comminuted by any suitable device, such as by subjecting the algae to sonic vibrations in water.

It is preferred that the dried algal powder be extracted to provide an effective concentration of the active components for topical application by combining the powder with water in proportions on the order of from 100 parts by weight water to 1 part by weight of powder (50 mg of powder to 5 ml of water). If the algae were not first dried, the amount of water employed for extraction can be adjusted to compensate for the natural water content of the plant, which is on the order of 90% by weight.

The aqueous extract is preferably sterilized by passing it through a conventional millipore filter or other suitable system for separating bacterial contaminants. In addition, or alternatively, the water soluble extract can be mixed with suitable preservatives such as glycerine or ethanol in weight proportions on the order of one part by weight of extract to one part by weight of preservative. In the sterilized and preserved form, the extract is maintained in its active state for an indefinite period when kept in a stoppered or closed container.

It has been found that the water soluble extract from the aforementioned marine red algae is effective to inhibit replication of the herpes virus in humans affected with the same, especially when the virus manifests itself in the form of herpetic gingiva stomatitis, herpes zoster, and herpetic lesions, such as cold sores. It is also believed that the active compositions of matter in the water soluble extract for efficacious to inhibit replication of the herpes virus manifesting itself in herpetic infections of the eye (herpes keratitis), varicella lesions, genital herpetic infections and herpetic infections in the fetus and newly born children. The water soluble extract from the aforementioned marine red algae has been found to be more effective when the extract is applied soon after the viral infection manifests itself in the form of tenderness, subcutaneous inflammation, or a surface lesion on the skin or other tissue, but most preferably before the lesion develops.

The method of treatment utilizing the water soluble extract of the present invention can generally be by topical application of the water soluble algal extract. For the treatment of cold sores or fever blisters attributable to the herpes virus, the water soluble extract is directly contacted with the infected area. Normally the frequency of application is at 20 minute to 30 minute intervals during the first few hours of treatment. Thereafter, the affected areas can be treated topically at one hour intervals or as often as necessary to maintain continuity of pain relief. When the water soluble algal extract of the present invention is mixed in weight proportions on the order of 1:1 with glycerine or with ethanol, the efficacy of the algal extract remains substantially the same.

For herpetic infections of the mouth and throat (for example, canker cores and herpetic vesicular stomatitis), the same topical application as for cold sores is preferred. It is further preferred that the water soluble algal extract prepared as set forth above be used without dilution with glycerine or ethanol. For limited outbreaks (when only a few lesions appear on the skin), the extract is applied topically with a swab or other suitable applicator. The same intervals for application are used as were used for cold sores. For extensive outbreaks of herpetic infection, it is preferred that the solution is used as a mouthwash. Again, the same application intervals are preferred as for cold sores.

For the treatment of herpes zoster, the undiluted extract is again preferred for application at the same intervals. When the water soluble algal extract is used to treat external genital herpes, the extract would be applied to the affected area with a swab or other suitable applicator. Again, the same intervals for application would be used as for cold sores.

It is also believed that the active components of the water soluble extract can be used for systemic treatment of nonsurface manifestations of herpes viruses, such as herpetic encephalitis. Such treatment can be effected by using purified extracts of the active components in a suitable carrier administered intravenously, by inhalation or by oral ingestion to a person infected with the herpes virus.

EXAMPLE

The following Example is intended to illustrate the efficacy of the water soluble algal extract, as well as to instruct one of ordinary skill in the art how to extract and use the active components from the marine red algae identified above. The Example is not intended to in any way limit the scope of the disclosed invention.

EXAMPLE

Red marine algae identified as *Neodilsea americana* is dried for 8 to 12 hours at room temperature. Thereafter, the partially dried algae is further dried for about 10 minutes at 120° F. in an oven. The dried algae is then ground to a powder with a mortar and pestle. 500 mg portions of the algal powder are placed in each of 2 or 3 50 ml vials. To prepare the powder for application, the contents of a vial are mixed with about 50 ml of distilled water, stirred and allowed to set for about 30 minutes to yield an aqueous solution of the water soluble algal extract.

A human had symptoms on the lower trunk on both sides of the body and including the groin, which symptoms were excruciating pain, blisters, and difficulty in walking due to blisters in the groin area. The patient had been diagnosed as having herpes zoster.

The patient was first treated several days after onset of symptoms with the aqueous solution of the water soluble extract from the algae powder prepared as described above with distilled water. The patient was treated topically by applying the aqueous solution of the algal extract with a cotton swab directly on the blisters, both broken and unbroken, and on areas which were painful but showed no sign of blistering. The aqueous solution of the algae extract was applied to only one side of the body, leaving the other side untreated, with the exception that the entire groin was treated. The algae extract was applied to the treated area at approximately hourly intervals.

On the treated area, a slight soothing effect was felt within a half hour, and within an hour the patient stated the pain in the surface areas had been reduced by half. The pain deep in the groin was not affected.

Treatment was continued by topical application several times daily. Within about three days the blisters on the treated side had dried up and were healing, and the pain had ceased. On the untreated side the blisters were still present and painful. After the originally treated side was essentially healed, the other, untreated area was treated in the manner of the first treated area. This newly treated side then followed the same course of healing as the side first treated; that is, within about three days of first application of the algae extract, the blisters were dried up and healing, and the pain was gone.

Although the present invention has been described in relation to a preferred embodiment, it is to be understood that one of ordinary skill may make various changes, substitutions of equivalents and other alterations without departing from the scope of the invention as disclosed. It is therefore intended that the grant of Letters Patent hereon be limited only by the definition contained in the appended claims and equivalents thereof.

The embodiments of the invention in which an exclusive property or privilege is claimed are defined as follows:

1. A method of treating and relieving pain of herpetic virus infections in humans comprising the steps of:
   intimately contacting the surface region directly infected with said virus with a water soluble extract of a marine red algae selected from the group consisting of *Neodilsea americana* and *Neodilsea integra* and mixtures thereof.

2. The method of claim 1 wherein said alga consists essentially of *Neodilsea americana*.

3. The method of claim 1 wherein said alga consists essentially of *Neodilsea integra*.

* * * * *